US006660485B2

(12) United States Patent
Lal et al.

(10) Patent No.: US 6,660,485 B2
(45) Date of Patent: Dec. 9, 2003

(54) ANTIBODIES TO HUMAN GOOSE-TYPE LYSOZYME

(75) Inventors: Preeti Lal, Santa Clara, CA (US); Karl J. Guegler, Menlo Park, CA (US); Neil C. Corley, Mountain View, CA (US); Chandra Patterson, Mountain View, CA (US)

(73) Assignee: Incyte Corporation, Palo Alto, CA (US)

( * ) Notice: Subject to any disclaimer, the term of this patent is extended or adjusted under 35 U.S.C. 154(b) by 80 days.

(21) Appl. No.: 09/844,036

(22) Filed: Apr. 26, 2001

(65) Prior Publication Data

US 2002/0106704 A1 Aug. 8, 2002

Related U.S. Application Data

(62) Division of application No. 09/511,720, filed on Feb. 23, 2000, now Pat. No. 6,268,164, which is a division of application No. 09/105,567, filed on Jun. 26, 1998, now Pat. No. 6,083,700.

(51) Int. Cl.[7] .................. G01N 33/53; C07K 16/46; C07K 16/40

(52) U.S. Cl. ............ 435/7.1; 530/387.3; 530/387.9; 530/388.26; 530/387.1; 530/391.1; 424/146.1

(58) Field of Search ............ 530/387.9, 388.26, 530/389.1; 435/70.21, 7.1, 387.3, 391.1; 424/146.1

(56) References Cited

U.S. PATENT DOCUMENTS

| 5,786,163 A | * | 7/1998 | Hall |
| 6,083,700 A | * | 7/2000 | Lal et al. |
| 6,268,164 B1 | * | 7/2001 | Lal et al. |

FOREIGN PATENT DOCUMENTS

| WO | WO 99/58642 | 5/1999 |

OTHER PUBLICATIONS

Lederman S, et al. A Single amino acid substitution in a common African allele of the CD4 molecule ablates binding of the monclonal antibody, OKT4. Mol Immunol. 28(11):1171–81, 1991.*
Colman PM. Effects of amino acid sequence changes on antibody–antigen interactions. Res Immnuol. 145(1):33–36, 1994.*
Li CH, Yamashiro D, Tseng LF, Chang WC, Ferrara P. beta–Endorphin omission analogs: dissociation of immunoreactivity from other biological activites. Proc Natl Acad Sci U S A. 77(6):3211–3214, 1980.*
Bendayan M. Possibilities of false immunocytochemical results generated by the use of monclonal antibodies: the example o the anti–proinsulin antibody. J Histochem Cytochem. 43(9);881–6, 1995.*
Owens RJ, Young RJ. The genetic engineering of monoclonal antibodies. J Immunol Methods. 168(2):149–165, 1994.*
Bird RE, Hardman KD, Jacobson JW, Johnson S, Kaufman BM, Lee SM, Lee T, Pope SH, Riordan GS, Whitlow M. Single–chain antigen–binding proteins. Science. 242(4877):423–426 (1988).*
Harlow E, Lane D.. Antibodies a laboratory manual. Cold Spring Harbor, New York: Cold Spring Harbor Laboratory Press, 1989.*
Online Mendelian Inheritance in Man (OMIM) #153450 Lysozyme, 1999.
Weaver, L.H. et al., "Structure of Phage P22 Gene 19 Lysozyme Inferral from its Homology with Phage T4 Lysozyme Implications for Lysozyme Evolution", *J. Mol. Biol.*, 184: 739–741 (1985).
Nakano, T. and T. Graf, "Goose–type lysozyme gene of the chicken: sequence genomic organization and expression reveals major difference to chicken–type lysozyme gene", *Biochim. Biophys. Acta*, 1090: 273–276 (1991).
Graf, T., (Direct Submission), GenBank Sequence Database (Accession X61002), National Center for Biotechnology Information, National Library of Medicine, Bethesda, Maryland, 20894 (GI 63427; GI 63428), 1992.
Shinagawa, S. et al., (Direct Submission), GenBank Sequence Database (Accession 1310929), National Center for Biotechnology Information, National Library of Medicine, Bethesda, Maryland, 20894 (GI 1310929), 1998.
Yoshimura K. et al., "Human Lysozyme: Sequence of a cDNA, and expression and Secretion by *Saccharomyces cerevisiae*", *Biochem. Biophys. Res. Commun.*, 150: 794–801 (1988).
Pepys, M.B. et al., "Human lysozyme gene mutations cause hereditary systemic amyloidosis", *Nature*, 362: 553–557 (1993).
Online Mendelian Inheritance in Man (OMIM) #105200 Familial Visceral Amyloidosis, 2001.
Cotran, R.S. et al., *Robbins: Pathologic Basis of Disease*, W.B. Saunders Company, Philadelphia, PA, pp. 231–238 (1994).
Nakano, T. and T. Graf, "Identification of genes differentially expressed in two type of v–myb–transformed avian myelomonocytic cells", *Oncogene*, 7: 527–534 (1992).
Enzymatic Assay of Lysozyme1, Sigma Aldrich, St. louis, MO, 1996.
Hillier et al. Wash U–NCI human EST project, Accession No.: AA779725, dated Feb. 5, 1998.

(List continued on next page.)

Primary Examiner—Christina Chan
Assistant Examiner—Maher Haddad
(74) *Attorney, Agent, or Firm*—Incyte Corporation

(57) ABSTRACT

The invention provides a human goose-type lysozyme (GOLY) and polynucleotides which identify and encode GOLY. The invention also provides expression vectors, host cells, antibodies, agonists, and antagonists. The invention also provides methods for diagnosing, treating or preventing disorders associated with expression of GOLY.

13 Claims, 4 Drawing Sheets

OTHER PUBLICATIONS

Hillier et al. Wash U–NCI human EST project, Accession No.: AA451707, Jun. 5, 1997.
Hillier et al. Wash U–NCI human EST project, Accession No.: AA453324, Jun. 5, 1997.
Maniatis et al. Molecular cloning ColdSpring Harbor Press, 1982, pp. 382–389 (1982).

Hagenbuchle, O. and Wellauer, P.K., "A rapid method for the isolation of DNA–binding proteins from purified nuceli of tissues and cells in culture", *Nucleic Acids Res.* 20(14): 3555–3559 (1992).

\* cited by examiner

```
                    10              19          28              37              46              55
5' T TGC TAT GTT GCC CAG GCT GGT CTT GAA GTG CCT CCT TGA CCT CCT AAA GTG TTG GAA
     64              73              82              91              100             109
CCA CAG ACG TGA GCC ACT CCA CCC AGC CTA AAA CTT CAT CTT TGG ATG AGA
     118             127             136             145             154             163
TGA ACA CTT TTA ACA AGA GAA CAG GAC TCT ATA TAA ATC GCT GTG GGC TCA CCA
     172             181             190             199             208             217
CCT CTA AGG AGC ACT GAC TGA AGA CAG AAA AAT TGA TGA ACT GAA GAA GAC
     226             235             244             253             262             271
ATG GTC CAT TAT GCC TTA CAA ACT TAC ACA GTG CTT TGG GAA TTC CAA AGT ACT
     280             289             298             307             316             325
CAG TGG AGA GAG GTG TTT CAG GAG CCG TAG AGC CAG ATC GTC ATC ATG TCT GCA
                                                                     M   S   A
     334             343             352             361             370             379
TTG TGG CTG CTG CTG GGC CTC CTT GCC CTG ATG GAC TTG TCT GAA AGC AGC AAC
 L   W   L   L   L   G   L   L   A   L   M   D   L   S   E   S   S   N
```

FIGURE 1A

```
TGG GGA TGC TAT GGA AAC ATC CAA AGC CTG GAC ACC CCT GGA GCA TCT TGT GGG
    388         397         406         415         424         433
 W   G   C   Y   G   N   I   Q   S   L   D   T   P   G   A   S   C   G

ATT GGA AGA CGT CAC GGC CTG AAC TAC TGT GGA GTT CGT GCT TCT GAA AGG CTG
    442         451         460         469         478         487
 I   G   R   R   H   G   L   N   Y   C   G   V   R   A   S   E   R   L

GCT GAA ATA GAC ATG CCA TAC CTC AAA TAT CAA CCC ATG CAA ACC ATT
    496         505         514         523         532         541
 A   E   I   D   M   P   Y   L   K   Y   Q   P   M   Q   T   I

GGC CAA AAG TAC TGC ATG GAT CCT GCC GTG ATC GCT GGT GTC TTG TCC AGG AAG
    550         559         568         577         586         595
 G   Q   K   Y   C   M   D   P   A   V   I   A   G   V   L   S   R   K

TCT CCC GGT GAC AAA ATT CTG GTC AAC ATG GGC GAT AGG ACT AGC ATG GTG CAG
    604         613         622         631         640         649
 S   P   G   D   K   I   L   V   N   M   G   D   R   T   S   M   V   Q

GAC CCT GGC TCT CAA GCT CCC ACA TCC TGG ATT AGT GAG TCT CAG GTT TCC CAG
    658         667         676         685         694         703
 D   P   G   S   Q   A   P   T   S   W   I   S   E   S   Q   V   S   Q

ACA ACT GAA GTT CTG ACT ACT AGA ATC AAA GAA ATC CAG AGG TTT CCA ACC
    712         721         730         739         748         757
 T   T   E   V   L   T   T   R   I   K   E   I   Q   R   F   P   T
```

FIGURE 1B

```
        766           775           784           793       802           811
TGG ACC CCT GAC CAG TAC CTG AGA GGT GGA CTC TGT GCC TAC AGT GGG GGT GCT
 W   T   P   D   Q   Y   L   R   G   G   L   C   A   Y   S   G   G   A
        820           829           838           847       856           865
GGC TAT GTC CGA AGC AGC CAG GAC CTG AGC TGT GAC TTC TGC AAT GAT GTC CTT
 G   Y   V   R   S   S   Q   D   L   S   C   D   F   C   N   D   V   L
        874           883           892           901       910           919
GCA CGA GCC AAG TAC CTC AAG AGA CAT GGC TTC TAA CAT CTC AGA TGA AAC CCA
 A   R   A   K   Y   L   K   R   H   G   F
        928           937           946           955       964           973
AGA CCA TGA TCA CAT ATG CAG CCT CAA ATG TTA CAC AGA TAA AAC TAG CCA AGG
        982           991           1000          1009      1018          1027
GCA CCT GTA ACT GGG AAT CTG AGT TTG ACC TAA AAG TCA TTA AAA TAA CAT GAA
        1036          1045
TCA CAT TAA AGG AAG AAT T 3'
```

ANTIBODIES TO HUMAN GOOSE-TYPE LYSOZYME

This application is a divisional application of U.S. application Ser. No. 09/511,720, filed Feb. 23, 2000, now U.S. Pat. No. 6,268,164, issued Jul. 31, 2001, which is a divisional application of U.S. application Ser. No. 09/105,567, filed Jun. 26, 1998, now U.S. Pat. No. 6,083,700, issued Jul. 4, 2000, all of which applications and patents are hereby incorporated herein by reference.

FIELD OF THE INVENTION

This invention relates to nucleic acid and amino acid sequences of a human goose-type lysozyme and to the use of these sequences in the diagnosis, treatment, and prevention of autoimmune/inflammatory, renal, and adrenal disorders and cancer.

BACKGROUND OF THE INVENTION

Lysozymes are a family of enzymes that catalyze the hydrolysis of certain mucopolysaccharides of bacterial cell walls, specifically the beta (1-4) glycosidic linkages between N-acetylmuramic acid and N-acetylglucosamine, and cause bacterial lysis. Lysozymes occur in diverse organisms including viruses, birds, and mammals. In humans, lysozymes are found in spleen, lung, kidney, white blood cells, plasma, saliva, milk, tears, and cartilage. (Online Mendelian Inheritance in Man (OMIM) #153450 Lysozyme; Weaver, L. H. et al. (1985) J. Mol. Biol. 184:739–741.)

The two known forms of lysozymes, chicken-type and goose-type, were originally isolated from chicken and goose egg white, respectively. Chicken-type and goose-type lysozymes have similar three-dimensional structures but different amino acid sequences. (Nakano, T. and Graf, T. (1991) Biochim. Biophys. Acta 1090:273–276.) In chickens both forms of lysozyme are found in neutrophil granulocytes (heterophils), but only chicken-type lysozyme is found in egg white. An analysis of the expression pattern of chicken-type and goose-type lysozyme mRNA in chicken was performed. Chicken-type lysozyme mRNA is found in both adherent monocytes and macrophages and nonadherent promyelocytes and granulocytes as well as cells of the bone marrow, spleen, bursa, and oviduct. Goose-type lysozyme mRNA is found in non-adherent cells of the bone marrow and lung. The goose-type lysozyme gene cloned from chicken encodes a 211 amino acid protein containing a putative 26 amino acid N-terminal cleavable signal sequence. Homologous goose-type lysozymes are found in chicken, black swan, goose, and ostrich. Conserved residues include the three catalytic center residues Glu99, Asp112, and Asp123 (numbering from the chicken goose-type lysozyme precursor) and four cysteines that are known to form two disulfide bonds in the black swan goose-type lysozyme. Several isozymes have been found in rabbits, including leukocytic, gastrointestinal, and possibly lymphoepithelial forms. (OMIM #153450, supra; Nakano (1991) supra; and GenBank g1310929.) A human lysozyme gene has been cloned that encodes a protein that is similar to chicken-type lysozyme. (Yoshimura, K. et al. (1988) Biochem. Biophys. Res. Commun. 150:794–801.)

Lysozymes have several disease associations. Nakano (supra) suggested a role for lysozyme in host defense systems. Older rabbits with an inherited lysozyme deficiency show increased susceptibility to infections, especially subcutaneous abscesses. (OMIM #153450, supra.) Human lysozyme gene mutations cause hereditary systemic amyloidosis, a rare autosomal dominant disease in which amyloid deposits form in the viscera, including the kidney, adrenal glands, spleen, and liver. This disease is usually fatal by the fifth decade. The amyloid deposits contain lysozyme with amino-acid substitutions. Renal amyloidosis is the most common and potentially the most serious form of organ involvement. (Pepys, M. B. et al. (1993) Nature 362:553–557; OMIM #105200 Familial Visceral Amyloidosis; Cotran, R. S. et al. (1994) *Robbins Pathologic Basis of Disease*, W. B. Saunders Company, Philadelphia, Pa., pp. 231–238.) Goose-type lysozyme is expressed in avian promyelocytes transformed with avian myeloblastosis virus containing the L106 mutant form of the v-myb oncogene. (Nakano, T. and Graf. T. (1992) Oncogene 7:527–534; and Nakano (1991) supra.)

The discovery of a new human goose-type lysozyme and the polynucleotides encoding it satisfies a need in the art by providing new compositions which are useful in the diagnosis, treatment, and prevention of autoimmune/inflammatory, renal, and adrenal disorders and cancer.

SUMMARY OF THE INVENTION

The invention is based on the discovery of a new human goose-type lysozyme (GOLY), the polynucleotides encoding GOLY, and the use of these compositions for the diagnosis, treatment, or prevention of autoimmune/inflammatory, renal, and adrenal disorders and cancer.

The invention features a substantially purified polypeptide comprising the amino acid sequence of SEQ ID NO:1 or a fragment of SEQ ID NO:1.

The invention further provides a substantially purified variant having at least 90% amino acid sequence identity to the amino acid sequence of SEQ ID NO: 1 or a fragment of SEQ ID NO: 1. The invention also provides an isolated and purified polynucleotide encoding the polypeptide comprising the sequence of SEQ ID NO: 1 or a fragment of SEQ ID NO: 1. The invention also includes an isolated and purified polynucleotide variant having at least 70% polynucleotide sequence identity to the polynucleotide encoding the polypeptide comprising the amino acid sequence of SEQ ID NO: 1 or a fragment of SEQ ID NO: 1.

The invention further provides an isolated and purified polynucleotide which hybridizes under stringent conditions to the polynucleotide encoding the polypeptide comprising the amino acid sequence of SEQ ID NO: 1 or a fragment of SEQ ID NO: 1, as well as an isolated and purified polynucleotide which is complementary to the polynucleotide encoding the polypeptide comprising the amino acid sequence of SEQ ID NO: 1 or a fragment of SEQ ID NO: 1.

The invention also provides an isolated and purified polynucleotide comprising the polynucleotide sequence of SEQ ID NO:2 or a fragment of SEQ ID NO:2, and an isolated and purified polynucleotide variant having at least 70% polynucleotide sequence identity to the polynucleotide comprising the polynucleotide sequence of SEQ ID NO:2 or a fragment of SEQ ID NO:2. The invention also provides an isolated and purified polynucleotide having a sequence complementary to the polynucleotide comprising the polynucleotide sequence of SEQ ID NO:2 or a fragment of SEQ ID NO:2.

The invention further provides an expression vector comprising at least a fragment of the polynucleotide encoding the polypeptide comprising the sequence of SEQ ID NO:1 or a fragment of SEQ ID NO:1. In another aspect, the expression vector is contained within a host cell.

The invention also provides a method for producing a polypeptide comprising the amino acid sequence of SEQ ID NO:1 or a fragment of SEQ ID NO:1, the method comprising the steps of: (a) culturing the host cell comprising an expression vector containing at least a fragment of a polynucleotide encoding the polypeptide comprising the amino acid sequence of SEQ ID NO:1 or a fragment of SEQ ID NO:1 under conditions suitable for the expression of the polypeptide; and (b) recovering the polypeptide from the host cell culture.

The invention also provides a pharmaceutical composition comprising a substantially purified polypeptide having the sequence of SEQ ID NO:1 or a fragment of SEQ ID NO:1 in conjunction with a suitable pharmaceutical carrier.

The invention further includes a purified antibody which binds to a polypeptide comprising the sequence of SEQ ID NO:1 or a fragment of SEQ ID NO:1, as well as a purified agonist and a purified antagonist of the polypeptide.

The invention also provides a method for treating or preventing an autoimmune/inflammatory disorder, the method comprising administering to a subject in need of such treatment an effective amount of a pharmaceutical composition comprising substantially purified polypeptide having the amino acid sequence of SEQ ID NO:1 or a fragment of SEQ ID NO:1.

The invention also provides a method for treating or preventing a renal disorder, the method comprising administering to a subject in need of such treatment an effective amount of a pharmaceutical composition comprising substantially purified polypeptide having the amino acid sequence of SEQ ID NO:1 or a fragment of SEQ ID NO:1.

The invention also provides a method for treating or preventing an adrenal disorder, the method comprising administering to a subject in need of such treatment an effective amount of a pharmaceutical composition comprising substantially purified polypeptide having the amino acid sequence of SEQ ID NO:1 or a fragment of SEQ ID NO:1.

The invention also provides a method for treating or preventing a cancer, the method comprising administering to a subject in need of such treatment an effective amount of an antagonist of the polypeptide having the amino acid sequence of SEQ ID NO:1 or a fragment of SEQ ID NO:1.

The invention also provides a method for detecting a polynucleotide encoding a polypeptide comprising the amino acid sequence of SEQ ID NO:1 or a fragment of SEQ ID NO:1 in a biological sample containing nucleic acids, the method comprising the steps of: (a) hybridizing the complement of the polynucleotide encoding the polypeptide comprising the amino acid sequence of SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding the polypeptide comprising the amino acid sequence of SEQ ID NO:1 or a fragment of SEQ ID NO:1 in the biological sample. In one aspect, this method further comprises amplifying the polynucleotide prior to the hybridizing step.

BRIEF DESCRIPTION OF THE FIGURES AND TABLES

FIGS. 1A, 1B, and 1C show the amino acid sequence (SEQ ID NO:1) and nucleic acid sequence (SEQ ID NO:2) of GOLY. The alignment was produced using MACDNASIS PRO software (Hitachi Software Engineering, South San Francisco, Calif.).

FIG. 2 shows the amino acid sequence alignment between GOLY (2372794; SEQ ID NO:1), chicken goose-type lysozyme (GI 63428; SEQ ID NO:7), produced using the multisequence alignment program of LASERGENE software (DNASTAR Inc, Madison Wis.).

Table 1 shows the programs, algorithms, databases and cutoff scores (when appropriate) used to identify and characterize GOLY.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

DEFINITIONS

"GOLY" refers to the amino acid sequences, or variant thereof, of substantially purified GOLY obtained from any species, particularly a mammalian species, including bovine, ovine, porcine, murine, equine, and preferably the human species, from any source, whether natural, synthetic, semi-synthetic, or recombinant.

The term "agonist" refers to a molecule which, when bound to GOLY, increases or prolongs the duration of the effect of GOLY. Agonists may include proteins, nucleic acids, carbohydrates, or any other molecules which bind to and modulate the effect of GOLY.

An "allelic variant" is an alternative form of the gene encoding GOLY. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding GOLY include those sequences with deletions, insertions, or substitutions of different nucleotides, resulting in a polynucleotide the same as GOLY or a polypeptide with at least one functional characteristic of GOLY. Included within this definition are polymorphisms which may or may not be readily detectable using a particular oligonucleotide probe of the polynucleotide encoding GOLY, and improper or unexpected hybridization to allelic variants, with a locus other than the normal chromosomal locus for the polynucleotide sequence encoding GOLY. The encoded protein may also be "altered," and may contain deletions, insertions, or substitutions of amino acid residues which produce a silent change and result in a functionally equivalent GOLY. Deliberate amino acid substitutions may be made on the basis of similarity in polarity, charge, solubility, hydrophobicity, hydrophilicity, and/or the amphipathic nature of the residues, as long as the biological or immunological activity of GOLY is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence" refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of GOLY which are preferably at least 5 to about 15 amino acids in length, most preferably at least 14 amino acids, and which retain some biological activity or immunological activity of GOLY. Where "amino acid sequence" refers to an amino acid sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which, when bound to GOLY, decreases the amount or the duration of the effect of the biological or immunological activity of GOLY. Antagonists may include proteins, nucleic acids, carbohydrates, antibodies, or any other molecules which decrease the effect of GOLY.

The term "antibody" refers to intact molecules as well as to fragments thereof, such as Fab, $F(ab')_2$, and Fv fragments, which are capable of binding the epitopic determinant. Antibodies that bind GOLY polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

The term "biologically active," refers to a protein having structural, regulatory, or biochemical functions of a naturally occurring molecule. Likewise, "immunologically active" refers to the capability of the natural, recombinant, or synthetic GOLY, or of any oligopeptide thereof, to induce a specific immune response in appropriate animals or cells and to bind with specific antibodies.

The terms "complementary" or "complementarity" refer to the natural binding of polynucleotides by base pairing. For example, the sequence "5' A-G-T 3'" binds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence" refer broadly to any composition containing the given polynucleotide or amino acid sequence. The composition may comprise a dry formulation or an aqueous solution. Compositions comprising polynucleotide sequences encoding GOLY or fragments of GOLY may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g., sodium dodecyl sulfate (SDS), and other components, e.g., Denhardt's solution, dry milk, salmon sperm DNA, etc. "Consensus sequence" refers to a nucleic acid sequence which has been resequenced to resolve uncalled bases, extended using XL-PCR kit (Applied Biosystems, Foster City, Calif.) in the 5' and/or the 3' direction, and resequenced, or which has been assembled from the overlapping sequences of more than one Incyte Clone using a computer program for fragment assembly, such as the GELVIEW fragment assembly system (GCG, Madison, Wis.). Some sequences have been both extended and assembled to produce the consensus sequence.

The term "correlates with expression of a polynucleotide" indicates that the detection of the presence of nucleic acids, the same or related to a nucleic acid sequence encoding GOLY, by Northern analysis is indicative of the presence of nucleic acids encoding GOLY in a sample, and thereby correlates with expression of the transcript from the polynucleotide encoding GOLY.

A "deletion" refers to a change in the amino acid or nucleotide sequence that results in the absence of one or more amino acid residues or nucleotides.

The term "derivative" refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity" refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Inc., Madison Wis.). The MEGALIGN program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs) are linear microchromosomes which may contain DNA sequences of about 6 kb to 10 Mb in size, and which contain all of the elements required for stable mitotic chromosome segregation and maintenance.

The term "humanized antibody" refers to antibody molecules in which the amino acid sequence in the non-antigen binding regions has been altered so that the antibody more closely resembles a human antibody, and still retains its original binding ability.

"Hybridization" refers to any process by which a strand of nucleic acid bonds with a complementary strand through base pairing.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition" refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray" refers to an arrangement of distinct polynucleotides arrayed on a substrate, e.g., paper, nylon or any other type of membrane, filter, chip, glass slide, or any other suitable solid support.

The terms "element" or "array element," in a microarray context, refer to hybridizable polynucleotides arranged on the surface of a substrate.

The term "modulate" refers to a change in the activity of GOLY. For example, modulation may cause an increase or a decrease in protein activity, binding characteristics, or any other biological, functional, or immunological properties of GOLY.

The phrases "nucleic acid" or "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked" refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. The term "oligonucleotide" is substantially equivalent to the terms "amplimer," "primer," "oligomer," and "probe," as these terms are commonly defined in the art.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell. (See, e.g., Nielsen, P. E. et al. (1993) Anticancer Drug Des. 8:53–63.)

The term "sample" is used in its broadest sense. A biological sample suspected of containing nucleic acids encoding GOLY, or fragments thereof, or GOLY itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

The terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of GOLY polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to GOLY. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

THE INVENTION

The invention is based on the discovery of a new human goose-type lysozyme (GOLY), the polynucleotides encoding GOLY, and the use of these compositions for the diagnosis, treatment, or prevention of autoimmune/inflammatory, renal, and adrenal disorders and cancer.

Nucleic acids encoding the GOLY of the present invention were first identified in Incyte Clone 2372794 from the adrenal gland cDNA library (ADRENOT07) using a computer search, e.g., BLAST, for amino acid sequence alignments. A consensus sequence, SEQ ID NO:2, was derived from the following overlapping and/or extended nucleic acid sequences: Incyte Clones 2372794HI (ADRENOT07), 3219266H1 (COLNNON03), and 2372794F6 and 2372794T6 (ADRENOT07) shown as SEQ ID NO:3–6 in the sequence.

In one embodiment, the invention encompasses a polypeptide comprising the amino acid sequence of SEQ ID NO:1, as shown in FIGS. 1A, 1B, and 1C. GOLY is 194 amino acids in length and has two potential casein kinase II phosphorylation sites at residues S94 and S170; and three potential protein kinase C phosphorylation sites at residues S54, S91, and T135. GOLY has a potential signal sequence from residue M1 through about residue S19. PRINTS analysis indicates that GOLY has sequence homology with the lysozyme G signature (PR00749) from residues C24 through H44, Y48 through Q69, M72 through L90, K139 through R155, G156 through D177, and D173 through G193. As shown in FIG. 2, GOLY has chemical and structural similarity with chicken goose-type lysozyme (GI 63428; SEQ ID NO:7). In particular, GOLY and chicken goose-type lysozyme share 39% identity. GOLY and chicken goose-type lysozyme share the four cysteines conserved in goose-type lysozymes that are proposed to form disulfide bonds at residues C24, C38, C49, and C80 of GOLY. GOLY contains the conserved goose-type lysozyme catalytic center aspartic acid residue at D105 and has a charged residue K93 and an acidic residue Q111, at the other two catalytic center residue sites. A fragment of SEQ ID NO:2 from about nucleotide 431 through about 447 is useful, for example, as a hybridization probe. Northern analysis shows the expression of this sequence in various libraries, at least 67% of which are immortalized or cancerous and at least 33% of which involve immune response. Of particular note is the expression of GOLY in kidney, breast, adrenal gland, and colon tissues.

The invention also encompasses GOLY variants. A preferred GOLY variant is one which has at least about 80%, more preferably at least about 90%, and most preferably at least about 95% amino acid sequence identity to the GOLY amino acid sequence, and which contains at least one functional or structural characteristic of GOLY.

The invention also encompasses polynucleotides which encode GOLY. In a particular embodiment, the invention encompasses a polynucleotide sequence comprising the sequence of SEQ ID NO:2, which encodes an GOLY.

The invention also encompasses a variant of a polynucleotide sequence encoding GOLY. In particular, such a variant polynucleotide sequence will have at least about 70%, more preferably at least about 85%, and most preferably at least about 95% polynucleotide sequence identity to the polynucleotide sequence encoding GOLY. A particular aspect of the invention encompasses a variant of SEQ ID NO:2 which has at least about 70%, more preferably at least about 85%, and most preferably at least about 95% polynucleotide sequence identity to SEQ ID NO:2. Any one of the polynucleotide variants described above can encode an amino acid sequence which contains at least one functional or structural characteristic of GOLY.

It will be appreciated by those skilled in the art that as a result of the degeneracy of the genetic code, a multitude of polynucleotide sequences encoding GOLY, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring GOLY, and all such variations are to be considered as being specifically disclosed.

Although nucleotide sequences which encode GOLY and its variants are preferably capable of hybridizing to the nucleotide sequence of the naturally occurring GOLY under appropriately selected conditions of stringency, it may be advantageous to produce nucleotide sequences encoding GOLY possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding GOLY and its derivatives without altering the encoded amino acid sequences include the production of RNA transcripts having more desirable properties, such as a greater half-life, than transcripts produced from the naturally occurring sequence.

The invention also encompasses production of DNA sequences which encode GOLY and GOLY derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding GOLY or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency. (See, e.g., Wahl, G. M. and S. L. Berger (1987) Methods Enzymol. 152:399–407; Kimmel, A. R. (1987) Methods Enzymol. 152:507–511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing and analysis are well known in the art. The methods may employ such enzymes as the Klenow fragment of DNA polymerase I, T7 SEQUENASE DNA polymerase, Taq DNA polymerase, THERMOSEQUENASE DNA polymerase (all from Amersham PB, Piscataway, N.J.), or combinations of polymerases and proofreading exonucleases, such as those found in the ELONGASE amplification system (Life Technologies, Gaithersberg, Md.). Preferably, sequence preparation is automated with machines, e.g., the ABI CATALYST 800 system (Applied Biosystems) or MICROLAB 2200 system (Hamilton, Reno, Nev.) systems, in combination with thermal cyclers. Sequencing can also be automated, such as by ABI PRISM 373 or 377 sequencing systems (PE Biosystems) or the MEGABACE 1000 sequencing system (Amersham PB). Sequences can be analyzed using computer programs and algorithms well known in the art. (See, e.g., Ausubel, supra, unit 7.7; and Meyers, R. A. (1995) *Molecular Biology and Biotechnology*, Wiley VCH, Inc, New York, N.Y.)

The nucleic acid sequences encoding GOLY may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–3060). Additionally, one may use PCR and nested primers to walk genomic DNA. This procedure avoids the need to screen libraries and is useful in finding intron/exon junctions. For all PCR-based methods, primers may be designed using commercially available software, such as OLIGO 4.06 primer analysis software (National Biosciences, Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR analysis software (PE Biosystems)), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode GOLY may be cloned in recombinant DNA molecules that direct expression of GOLY, or fragments or functional equivalents thereof, in appropriate host cells. Due to the inherent degeneracy of the genetic code, other DNA sequences which encode substantially the same or a functionally equivalent amino acid sequence may be produced and used to express GOLY.

The nucleotide sequences of the present invention can be engineered using methods generally known in the art in order to alter GOLY-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding GOLY may be synthesized, in whole or in part, using chemical methods well known in the art. (See, e.g., Caruthers, M. H. et al. (1980) Nucl. Acids Symp. Ser. (7) 215–223, and Horn, T. et al. (1980) Nucl. Acids Symp. Ser. (7) 225–232.) Alternatively, GOLY itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431A peptide synthesizer (PE Biosystems). Additionally, the amino acid sequence of GOLY, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, W H Freeman and Co., New York, N.Y.)

In order to express a biologically active GOLY, the nucleotide sequences encoding GOLY or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding GOLY. Such elements may vary in their strength and specificity. Specific initiation signals may also be used to achieve more efficient translation of sequences encoding GOLY. Such signals include the ATG initiation codon and adjacent sequences, e.g. the Kozak sequence. In cases where sequences encoding GOLY and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding GOLY and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding GOLY. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding GOLY. For example, routine cloning, subcloning, and propagation of polynucleotide sequences encoding GOLY can be achieved using a multifunctional *E. coli* vector such as PBLUESCRIPT phagemid (Stratagene) or PSPORT1 plasmid (Life Technologies). Ligation of sequences encoding GOLY into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of GOLY are needed, e.g. for the production of antibodies, vectors which direct high level expression of GOLY may be used. For example, vectors containing the strong, inducible T5 or T7 bacteriophage promoter may be used.

Yeast expression systems may be used for production of GOLY. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516–54; Scorer, C. A. et al. (1994) Bio/Technology 12:181–184.)

Plant systems may also be used for expression of GOLY. Transcription of sequences encoding GOLY may be driven viral promoters, e.g., the 35S and 19S promoters of CaMV used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., Hobbs, S. or Murry, L. E. in *McGraw Hill Yearbook of Science and Technology* (1992) McGraw Hill, New York, N.Y.; pp. 191–196.)

In mammalian cells, a number of viral-based expression systems may be utilized. In cases where an adenovirus is used as an expression vector, sequences encoding GOLY may be ligated into an adenovirus transcription/translation complex consisting of the late promoter and tripartite leader sequence. Insertion in a non-essential E1 or E3 region of the viral genome may be used to obtain infective virus which expresses GOLY in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nature Genet. 15:345–355.)

For long term production of recombinant proteins in mammalian systems, stable expression of GOLY in cell lines is preferred. For example, sequences encoding GOLY can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ or apr⁻ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides, neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP) (Clontech, Palo Alto, Calif.), β glucuronidase and its substrate β-D-glucuronoside, or luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding GOLY is inserted within a marker gene sequence, transformed cells containing sequences encoding GOLY can be identified by the absence of marker gene function. Alternatively, a marker gene can be placed in tandem with a sequence encoding GOLY under the control of a single promoter. Expression of the marker gene in response to induction or selection usually indicates expression of the tandem gene as well.

In general, host cells that contain the nucleic acid sequence encoding GOLY and that express GOLY may be identified by a variety of procedures known to those of skill in the art. These procedures include, but are not limited to, DNA—DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of GOLY using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on GOLY is preferred, but a competitive binding assay may be employed. These and other assays are well known in the art. (See, e.g., Hampton, R. et al. (1990) Serological Methods, a Laboratory Manual, APS Press, St Paul, Minn., Section IV; Coligan, J. E. et al. (1997 and periodic supplements) Current Protocols in Immunology, Greene Pub. Associates and Wiley-Interscience, New York, N.Y.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding GOLY include oligolabeling, nick translation, end-labeling, or PCR amplification using a labeled nucleotide. Alternatively, the sequences encoding GOLY, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham PB and Promega (Madison, Wis.). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding GOLY may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode GOLY may be designed to contain signal sequences which direct secretion of GOLY through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and W138), are available from the American Type Culture Collection (ATCC, Manassas Va.) and may be chosen to ensure the correct modification and processing of the foreign protein.

In another embodiment of the invention, natural, modified, or recombinant nucleic acid sequences encoding GOLY may be ligated to a heterologous sequence resulting in translation of a fusion protein in any of the aforementioned host systems. For example, a chimeric GOLY protein containing a heterologous moiety that can be recognized by a commercially available antibody may facilitate the screening of peptide libraries for inhibitors of GOLY activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the GOLY encoding sequence and the heterologous protein sequence, so that GOLY may be cleaved away from the heterologous moiety following purification. Methods for fusion protein expression and purification are discussed in Ausubel, F. M. et al. (1995 and periodic supplements) *Current Protocols in Molecular Biology*, John Wiley & Sons, New York, N.Y., ch 10. A variety of commercially available kits may also be used to facilitate expression and purification of fusion proteins.

In a further embodiment of the invention, synthesis of radiolabeled GOLY may be achieved in vitro using the TNT rabbit reticulocyte lysate or wheat germ extract systems (Promega). These systems couple transcription and translation of protein-coding sequences operably associated with the T7, T3, or SP6 promoters. Translation takes place in the presence of a radiolabeled amino acid precursor, preferably $^{35}S$-methionine.

Fragments of GOLY may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the ABI 431A peptide synthesizer (Applied Biosystems). Various fragments of GOLY may be synthesized separately and then combined to produce the full length molecule.

THERAPEUTICS

Chemical and structural similarity, e.g., in the context of sequences and motifs, exists between GOLY and goose-type lysozyme from chicken (GI 63428). In addition, GOLY is expressed in cancerous, inflamed, kidney, breast, adrenal gland, colon, and nervous tissues. Therefore, GOLY appears to play a role in autoimmune/inflammatory, renal, and adrenal disorders and cancer.

Therefore, in one embodiment, GOLY or a fragment or derivative thereof may be administered to a subject to treat or prevent an autoimmune/inflammatory disorder. Such autoimmune/inflammatory disorders can include, but are not limited to, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

In another embodiment, a vector capable of expressing GOLY or a fragment or derivative thereof may be administered to a subject to treat or prevent an autoimmune/ inflammatory disorder including, but not limited to, those described above.

In a further embodiment, a pharmaceutical composition comprising a substantially purified GOLY in conjunction with a suitable pharmaceutical carrier may be administered to a subject to treat or prevent an autoimmune/inflammatory disorder including, but not limited to, those provided above.

In still another embodiment, an agonist which modulates the activity of GOLY may be administered to a subject to treat or prevent an autoimmune/inflammatory disorder including, but not limited to, those listed above.

Therefore, in another embodiment, GOLY or a fragment or derivative thereof may be administered to a subject to treat or prevent a renal disorder. Such renal disorders can include, but are not limited to, renal amyloidosis, hypertension; primary aldosteronism; Addison's disease; renal failure; glomerulonephritis; chronic glomerulonephritis; tubulointerstitial nephritis; cystic disorders of the kidney and dysplastic malformations such as polycystic disease, renal dysplasias, and cortical or medullary cysts; inherited polycystic renal diseases (PRD) such as recessive and autosomal dominant PRD; medullary cystic disease; medullary sponge kidney and tubular dysplasia; Alport's syndrome; non-renal cancers which affect renal physiology, such as bronchogenic tumors of the lungs or tumors of the basal region of the brain; multiple myeloma; adenocarcinomas of the kidney; metastatic renal carcinoma; nephrotoxic disorders produced by the ingestion, injection, inhalation, or absorption of any pharmaceutical, chemical, or biological agent such as heavy metals, all classes of antibiotics, analgesics, solvents, oxalosis-inducing agents, anticancer drugs, herbicides and pesticides, botanicals and biologicals, and antiepileptics.

In another embodiment, a vector capable of expressing GOLY or a fragment or derivative thereof may be administered to a subject to treat or prevent a renal disorder including, but not limited to, those described above.

In a further embodiment, a pharmaceutical composition comprising a substantially purified GOLY in conjunction with a suitable pharmaceutical carrier may be administered to a subject to treat or prevent a renal disorder including, but not limited to, those provided above.

In still another embodiment, an agonist which modulates the activity of GOLY may be administered to a subject to treat or prevent a renal disorder including, but not limited to, those listed above.

Therefore, another embodiment, GOLY or a fragment or derivative thereof may be administered to a subject to treat or prevent an adrenal disorder. Such adrenal disorders can include, but are not limited to, hyperplasia, carcinoma, or adenoma of the adrenal cortex, hypertension associated with alkalosis, amyloidosis, hypokalemia, Cushing's disease, Liddle's syndrome, and Arnold-Healy-Gordon syndrome, pheochromocytoma tumors, and Addison's disease.

In another embodiment, a vector capable of expressing GOLY or a fragment or derivative thereof may be administered to a subject to treat or prevent an adrenal disorder including, but not limited to, those described above.

In a further embodiment, a pharmaceutical composition comprising a substantially purified GOLY in conjunction with a suitable pharmaceutical carrier may be administered to a subject to treat or prevent an adrenal disorder including, but not limited to, those provided above.

In still another embodiment, an agonist which modulates the activity of GOLY may be administered to a subject to treat or prevent an adrenal disorder including, but not limited to, those listed above.

In a further embodiment, an antagonist of GOLY may be administered to a subject to treat or prevent a cancer. Such a cancer may include, but is not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds GOLY may be used directly as an antagonist or indirectly as a targeting or delivery mechanism for bringing a pharmaceutical agent to cells or tissue which express GOLY.

In an additional embodiment, a vector expressing the complement of the polynucleotide encoding GOLY may be administered to a subject to treat or prevent a cancer including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of GOLY may be produced using methods which are generally known in the art. In particular, purified GOLY may be used to produce antibodies or to screen libraries of pharmaceutical agents to identify those which specifically bind GOLY. Antibodies to GOLY may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of polyclonal antibodies, various hosts including goats, rabbits, rats, mice, humans, and others may be immunized by injection with GOLY or with any fragment or oligopeptide thereof which has immunogenic properties. Rats and mice are preferred hosts for downstream applications involving monoclonal antibody production. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable. (For review of methods for antibody production and analysis, see, e.g., Harlow, E. and Lane, D. (1988) *Antibodies: A Laboratory Manual*, Cold Spring Harbor Laboratory, Cold Spring Harbor, N.Y.)

It is preferred that the oligopeptides, peptides, or fragments used to induce antibodies to GOLY have an amino acid sequence consisting of at least about 5 amino acids, and, more preferably, of at least about 14 amino acids. It is also preferable that these oligopeptides, peptides, or fragments are identical to a portion of the amino acid sequence of the natural protein and contain the entire amino acid sequence of a small, naturally occurring molecule. Short stretches of GOLY amino acids may be fused with those of another protein, such as KLH, and antibodies to the chimeric molecule may be produced.

Monoclonal antibodies to GOLY may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452454.) Alternatively, techniques described for the production of single chain antibodies may be adapted, using methods known in the art, to produce GOLY-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for GOLY may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity and minimal cross-reactivity. Numerous protocols for competitive binding or immunoradiometric assays using either polyclonal or monoclonal antibodies with established specificities are well known in the art. Such immunoassays typically involve the measurement of complex formation between GOLY and its specific antibody. A two-site, monoclonal-based immunoassay utilizing monoclonal antibodies reactive to two non-interfering GOLY epitopes is preferred, but a competitive binding assay may also be employed. (Maddox, supra.)

Various methods such as Scatchard analysis in conjunction with radioimmunoassay techniques may be used to assess the affinity of antibodies for GOLY. Affinity is expressed as an association constant, $K_a$, which is defined as the molar concentration of GOLY-antibody complex divided by the molar concentrations of free antigen and free antibody under equilibrium conditions. The $K_a$ determined for a preparation of polyclonal antibodies, which are heterogeneous in their affinities for multiple GOLY epitopes, represents the average affinity, or avidity, of the antibodies for GOLY. The $K_a$ determined for a preparation of monoclonal antibodies, which are monospecific for a particular GOLY epitope, represents a true measure of affinity. High-affinity antibody preparations with $K_a$ ranging from about $10^9$ to $10^{12}$ L/mole are preferred for use in immunoassays in which the GOLY-antibody complex must withstand rigorous manipulations. Low-affinity antibody preparations with $K_a$ ranging from about $10^6$ to $10^7$ L/mole are preferred for use in immunopurification and similar procedures which ultimately require dissociation of GOLY, preferably in active form, from the antibody. (Catty, D. (1988) *Antibodies, Volume I: A Practical Approach*, IRL Press, Washington, D. C.; and Liddell, J. E. and Cryer, A. (1991) *A Practical Guide to Monoclonal Antibodies*, John Wiley & Sons, New York, N.Y.)

The titre and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is preferred for use in procedures requiring precipitation of GOLY-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding GOLY, or any fragment or complement thereof, may be used for therapeutic purposes. In one aspect, the complement of the polynucleotide encoding GOLY may be used in situations in which it would be desirable to block the transcription of the mRNA. In particular, cells may be transformed with sequences complementary to polynucleotides encoding GOLY. Thus, complementary molecules or fragments may be used to modulate GOLY activity, or to achieve regulation of gene function. Such technology is now well known in the art, and sense or antisense oligonucleotides or larger fragments can be designed from various locations along the coding or control regions of sequences encoding GOLY.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding GOLY. (See, e.g., Sambrook, supra; and Ausubel, supra.)

Genes encoding GOLY can be turned off by transforming a cell or tissue with expression vectors which express high levels of a polynucleotide, or fragment thereof, encoding GOLY. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding GOLY. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding GOLY.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding GOLY. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of GOLY, antibodies to GOLY, and mimetics, agonists, antagonists, or inhibitors of GOLY. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of GOLY, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example GOLY or fragments thereof, antibodies of GOLY, and agonists, antagonists or inhibitors of GOLY, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind GOLY may be used for the diagnosis of disorders characterized by expression of GOLY, or in assays to monitor patients being treated with GOLY or agonists, antagonists, or inhibitors of GOLY. Antibodies useful for diagnostic purposes may be prepared in the same manner as described above for therapeutics. Diagnostic assays for GOLY include methods which utilize the antibody and a label to detect GOLY in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring GOLY, including ELISAs, RIAs, and FACS, are known in the art and provide a basis for diagnosing altered or abnormal levels of GOLY expression. Normal or standard values for GOLY expression are established by combining body fluids or cell extracts taken from normal mammalian subjects, preferably human, with antibody to GOLY under conditions suitable for complex formation. The amount of standard complex formation may be quantitated by various methods, preferably by photometric means. Quantities of GOLY expressed in subject, control, and disease samples from biopsied tissues are compared with the standard values. Deviation between standard and subject values establishes the parameters for diagnosing disease.

In another embodiment of the invention, the polynucleotides encoding GOLY may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of GOLY may be correlated with disease. The diagnostic assay may be used to determine absence, presence, and excess expression of GOLY, and to monitor regulation of GOLY levels during therapeutic intervention.

In one aspect, hybridization with PCR probes which are capable of detecting polynucleotide sequences, including genomic sequences, encoding GOLY or closely related molecules may be used to identify nucleic acid sequences which encode GOLY. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding GOLY, allelic variants, or related sequences.

Probes may also be used for the detection of related sequences, and should preferably have at least 50% sequence identity to any of the GOLY encoding sequences. The hybridization probes of the subject invention may be DNA or RNA and may be derived from the sequence of SEQ ID NO:2 or from genonic sequences including promoters, enhancers, and introns of the GOLY gene.

Means for producing specific hybridization probes for DNAs encoding GOLY include the cloning of polynucleotide sequences encoding GOLY or GOLY derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding GOLY may be used for the diagnosis of a disorder associated with expression of GOLY. Examples of such a disorder include, but are not limited to, autoimmune/inflammatory disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.; renal disorders such as renal amyloidosis, hypertension; primary aldosteronism; Addison's disease; renal failure; glomerulonephritis; chronic glomerulonephritis; tubulointerstitial nephritis; cystic disorders of the kidney and dysplastic malformations such as polycystic disease, renal dysplasias, and cortical or medullary cysts; inherited polycystic renal diseases (PRD) such as recessive and autosomal dominant PRD; medullary cystic disease; medullary sponge kidney and tubular dysplasia; Alport's syndrome; non-renal cancers which affect renal physiology, such as bronchogenic tumors of the lungs or tumors of the basal region of the brain; multiple myeloma; adenocarcinomas of the kidney; metastatic renal carcinoma; nephrotoxic disorders produced by the ingestion, injection, inhalation, or absorption of any pharmaceutical, chemical, or biological agent such as heavy metals, all classes of antibiotics, analgesics, solvents, oxalosis-inducing agents, anticancer drugs, herbicides and pesticides, botanicals and biologicals, and antiepileptics; adrenal disorders such as hyperplasia, carcinoma, or adenoma of the adrenal cortex, hypertension associated with alkalosis, amyloidosis, hypokalemia, Cushing's disease, Liddle's syndrome, and Arnold-Healy-Gordon syndrome, pheochromocytoma tumors, and Addison's disease; and cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The polynucleotide sequences encoding GOLY may be used in Southern or Northern analysis, dot blot, or other membrane-based technologies; in PCR technologies; in dipstick, pin, and ELISA-like assays; and in microarrays utilizing fluids or tissues from patients to detect altered GOLY expression. Such qualitative or quantitative methods are well known in the art.

In a particular aspect, the nucleotide sequences encoding GOLY may be useful in assays that detect the presence of associated disorders, particularly those mentioned above. The nucleotide sequences encoding GOLY may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding GOLY in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of GOLY, a normal or standard profile for expression is established. This may be accomplished by combining body fluids or cell extracts taken from normal subjects, either animal or human, with a sequence, or a fragment thereof, encoding GOLY, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding GOLY may involve the use of PCR. These oligomers may be chemically synthesized, generated enzymatically, or produced in vitro. Oligomers will preferably contain a fragment of a polynucleotide encoding GOLY, or a fragment of a polynucleotide complementary to the polynucleotide encoding GOLY, and will be employed under optimized conditions for identification of a specific gene or condition. Oligomers may also be employed under less stringent conditions for detection or quantitation of closely related DNA or RNA sequences.

Methods which may also be used to quantitate the expression of GOLY include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 212:229–236.) The speed of quantitation of multiple samples may be accelerated by running the assay in an ELISA-like format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding GOLY may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) Molecular Biology and Biotechnology, VCH Publishers New York, N.Y., pp. 965–968.) Examples of genetic map data can be found in various scientific journals or at the Online Mendelian Inheritance in Man (OMIM) site. Correlation between the location of the gene encoding GOLY on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, GOLY, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between GOLY and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with GOLY, or fragments thereof, and washed. Bound GOLY is then detected by methods well known in the art. Purified GOLY can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding GOLY specifically compete with a test compound for binding GOLY. In this manner, antibodies can be used to detect the presence of any peptide which shares one or more antigenic determinants with GOLY.

In additional embodiments, the nucleotide sequences which encode GOLY may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. ADRENOT07 cDNA Library Construction

The ADRENOT07 cDNA library was constructed from microscopically normal adrenal tissues obtained from a 61-year old Caucasian female. Pathology indicated no significant abnormality of the right and left adrenals. Patient history included the diagnosis of unspecified disorder of adrenal glands, depressive disorder, benign hypertension, vocal cord paralysis, hemiplegia, subarachnoid hemorrhage, communicating hydrocephalus, and neoplasm of uncertain behavior of pituitary gland and craniopharyngeal duct. Family history included malignant prostate neoplasm and malignant colon neoplasm.

The frozen tissue was homogenized and lysed using a POLYTRON homogenizer (PT-3000; Brinkmann Instruments, Westbury, N.Y.) in guanidinium isothiocyanate solution. The lysate was centrifuged over a 5.7 M CsCl cushion using a Beckman SW28 rotor in a Beckman L8-70M Ultracentrifuge (Beckman Coulter, Fullerton, Calif.) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and treated with DNase at 37° C. The RNA extraction and precipitation were repeated as before. The MRNA was isolated with the OLIGOTEX kit (Qiagen, Carlsbad, Calif.) and used to construct the cDNA library.

The mRNA was handled according to the recommended protocols in the SUPERSCRIPT plasmid system (Life Technologies). The cDNAs were fractionated on a SEPHAROSE CL4B column (Amersham PB), and those cDNAs exceeding 400 bp were ligated into pINCY plasmid (Incyte Genomics, Palo Alto). The plasmid pINCY was subsequently transformed into DH5α competent cells (Life Technologies).

II. Isolation of cDNA Clones

Plasmid DNA was released from the cells and purified using the REAL Prep 96 plasmid kit (Qiagen). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Life Technologies) with carbenicillin at 25 mg/l and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

III. Sequencing and Analysis

The cDNAs were prepared for sequencing using either an ABI CATALYST 800 (Applied Biosystems) or a MICROLAB 2200 system (Hamilton) in combination with DNA ENGINE thermal cyclers (MJ Research, Watertown, Mass.). The cDNAs were sequenced using ABI PRISM 373 or 377 sequencing systems (Applied Biosystems) by the method of Sanger F and A. R. Coulson (1975; J. Mol. Biol. 94:441–448) using standard ABI protocols, base calling software, and kits. Alternatively, cDNAs were sequenced using solutions and dyes from Amersham PB. Reading frame was determined using standard methods (Ausubel, supra).

The cDNA sequences presented in Table 1 and the full length nucleotide and amino acid sequences disclosed in the Sequence Listing were queried against databases such as GenBank primate (pri), rodent (rod), mammalian (mamp), vertebrate (vrtp), and eukaryote (eukp) databases, SwissProt, BLOCKS, and other databases which contain previously identified and annotated motifs and sequences. Algorithms such as Smith Waterman which deal with primary sequence patterns and secondary structure gap penalties (Smith, T. et al. (1992) Protein Engineering 5:35–51) and programs and algorithms such as BLAST (Basic Local Alignment Search Tool; Altschul, S. F. (1993) J. Mol. Evol 36:290–300; and Altschul et al. (1990) J. Mol. Biol. 215:403–410), and HMM (Hidden Markov Models; Eddy, S. R. (1996) Cur. Opin. Str. Biol. 6:361–365 and Sonnhammer, E. L. L. et al. (1997) Proteins 28:405–420) were used to assemble and analyze nucleotide and amino acid sequences. The databases, programs, algorithms, methods and tools are available, well known in the art, and described in Ausubel (supra, unit 7.7), in Meyers, R. A. (1995; *Molecular Biology and Biotechnology*, Wiley VCH, Inc, New York N.Y., p 856–853), in documentation provided with software (Genetics Computer Group (GCG), Madison Wis.), and on the world wide web (www). As shown in Table 1 (below), PFAM refers to both a database (http://genome.wustl.edu/Pfam/) and an HMM search tool (http://genome.wustl.edu/eddy/cgi-bin/hmmm_page.cgi).

TABLE 1 summarizes the databases and tools used to analyze GOLY. The first column of the table shows the tool, program, or algorithm; the second column, the database; the third column, a brief description; and the fourth column (where applicable), scores for determining the strength of a match between two sequences (the higher the value, the more homologous).

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST were used to search for identical or related molecules in nucleotide databases such as GenBank or LIFESEQ database (Incyte Genomics). This analysis is much faster than multiple membrane-based hybridizations. In addition, the sensitivity of the computer search can be modified to determine whether any particular match is categorized as exact or similar.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of northern analysis were reported as a list of libraries in which the transcript encoding GOLY occurs. Abundance, the number of times a particular transcript is represented in a cDNA library, and percent abundance, abundance divided by the total number of sequences, were reported.

V. Extension of GOLY Encoding Polynucleotides

The full-length nucleic acid sequence (SEQ ID NO:2) was produced by extension of its component fragments as described in The Invention section (supra) using oligonucleotide primers designed from those fragments. One primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer—primer dimerizations was avoided.

Selected human cDNA libraries (Life Technologies) were used to extend the sequence. If more than one extension is necessary or desired, additional sets of primers are designed to further extend the known region.

High fidelity amplification was obtained by following the instructions for the XL-PCR kit (Applied Biosystems) and thoroughly mixing the enzyme and reaction mix. PCR was performed using the DNA ENGINE thermal cycler (MJ Research), beginning with 40 pmol of each primer and the recommended concentrations of all other components of the kit, with the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using the QIAQUICK kit (Qiagen), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2× carb). The following day, several colonies were randomly picked from each plate and cultured in 150 µl of liquid LB/2× carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 are employed to screen cDNAs, genomic DNAs, or mRNAs.

Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 µCi of [γ-$^{32}$P] adenosine triphosphate (Amersham PB), and T4 polynucleotide kinase (NEN Life Science Products, Boston, Mass.). The labeled oligonucleotides are substantially purified using a SEPHADEX G-25 superfine size exclusion dextran bead column (Amersham PB). An aliquot containing $10^7$ counts per minute of the labeled probe is used in a typical membrane-based hybridization analysis of human genomic DNA digested with one of the following endonucleases: Ase I, Bgl II, Eco RI, Pst I, Xbal, or Pvu II (NEN Life Science Products).

The DNA from each digest is fractionated on a 0.7% agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Eastman Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the GOLY-encoding sequences, or any parts thereof, are used to detect, decrease, or inhibit expression of naturally occurring GOLY. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of GOLY. To inhibit transcription, a complementary oligonucleotide is designed from the most unique 5' sequence and used to prevent promoter binding to the coding sequence. To inhibit translation, a complementary oligonucleotide is designed to prevent ribosomal binding to the GOLY-encoding transcript.

IX. Expression of GOLY

Expression and purification of GOLY is achieved using bacterial or virus-based expression systems. For expression of GOLY in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express GOLY upon induction with isopropyl beta-D-thiogalactopyranoside (IPTG). Expression of GOLY in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding GOLY by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, GOLY is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from Schistosoma japonicum, enables the purification of fusion proteins on immobilized glutathione under conditions that maintain protein activity and antigenicity (Amersham PB). Following purification, the GST moiety can be proteolytically cleaved from GOLY at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (Qiagen). Methods for protein expression and purification are discussed in Ausubel, F. M. et al. (1995 and periodic supplements) *Current Protocols in Molecular Biology*, John Wiley & Sons, New York, N.Y., ch 10, 16. Purified GOLY obtained by these methods can be used directly in the following activity assay.

X. Demonstration of GOLY Activity

GOLY activity is demonstrated by the ability to lyse *Micrococcus lysodeikticus* bacterial cells. (Enzymatic Assay of Lysozyme 1, Sigma Aldrich, St. Louis Mo.). A 0.015% suspension of lyophilized *Micrococcus lysodeikticus* cells (ATCC 4698) is prepared in 66 mM potassium phosphate buffer, pH 6.24 (Buffer A) at 25° C. 2.5 ml of the cell suspension is pipetted into a optical cuvette and equilibrated to 25° C. The absorbance at 450 nm is monitored until constant, between 0.6 and 0.7, using a thermostatted spectrophotometer. A blank reaction is prepared in a second cuvette containing 2.5 ml Buffer A. GOLY is dissolved in cold Buffer A. 0.1 ml of the GOLY solution is added to the test cuvette, and 0.1 ml Buffer A is added to the blank cuvette. The cuvettes are immediately mixed by inversion, and the decrease in absorbance at 450 nm is recorded for approximately 5 minutes. As the bacteria lyse, the turbidity of the solution, and hence the absorbance at 450 nm, decrease. The rate of the decrease in absorbance at 450 nm in the test cuvette is proportional to the amount of GOLY in the original sample.

XI. Functional Assays

GOLY function is assessed by expressing the sequences encoding GOLY at physiologically elevated levels in mammalian cell culture systems. cDNA is subcloned into a mammalian expression vector containing a strong promoter that drives high levels of cDNA expression. Vectors of choice include PCMV SPORT (Life Technologies) and PCR 3.1 (Invitrogen, Carlsbad Calif.) plasmids, both of which contain the cytomegalovirus promoter. 5–10 μg of recombinant vector are transiently transfected into a human cell line, preferably of endothelial or hematopoietic origin, using either liposome formulations or electroporation. 1–2 μg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP) (Clontech), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry.*, Oxford, New York, N.Y.

The influence of GOLY on gene expression can be assessed using highly purified populations of cells transfected with sequences encoding GOLY and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of MRNA encoding GOLY and other genes of interest can be analyzed by Northern analysis or microarray techniques.

XII. Production of GOLY Specific Antibodies

GOLY substantially purified using polyacrylamide gel electrophoresis (PAGE)(see, e.g., Harrington, M.G. (1990) Methods Enzymol. 182:488495), or other purification techniques, is used to immunize rabbits and to produce antibodies using standard protocols.

Alternatively, the GOLY amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

ABI 431A Peptide synthesizer (PE Biosystems) using Fmoc-chemistry and coupled to KLH (Sigma Aldrich) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring GOLY Using Specific Antibodies

Naturally occurring or recombinant GOLY is substantially purified by immunoaffinity chromatography using antibodies specific for GOLY. An immunoaffinity column is constructed by covalently coupling anti-GOLY antibody to an activated chromatographic resin, such as CNBr-activated SEPHAROSE resin (Amersham PB). After the coupling, the resin is blocked and washed according to the manufacturer's instructions.

Media containing GOLY are passed over the immunoaffinity column, and the column is washed under conditions that allow the preferential absorbance of GOLY (e.g., high ionic strength buffers in the presence of detergent). The column is eluted under conditions that disrupt antibody/GOLY binding (e.g., a buffer of pH 2 to pH 3, or a high concentration of a chaotrope, such as urea or thiocyanate ion), and GOLY is collected.

XIV. Identification of Molecules Which Interact with GOLY

GOLY, or biologically active fragments thereof, are labeled with $^{125}$I Bolton-Hunter reagent. (See, e.g., Bolton et al. (1973) Biochem. J. 133:529–539.) Candidate molecules previously arrayed in the wells of a multi-well plate are incubated with the labeled GOLY, washed, and any wells with labeled GOLY complex are assayed. Data obtained using different concentrations of GOLY are used to calculate values for the number, affinity, and association of GOLY with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Program/algorithm | Databases | Description | Useful Parameters |
|---|---|---|---|
| ESTs | | | |
| Smith Waterman | GenBank | Local alignment algorithm for homology searching | min length = 49 nt <12% uncalled bases |
| FASTA | GenBank | Fast nucleotide sequence database searching program for UNIX, VMS | |
| BLAST | GenBank | Ultra-fast database searching program for UNIX, VMS C source | Log likelihood for exact matches is ~$10^{25}$ and for homologs >$10^8$ |
| Full Length | | | |
| Phred | | Reads trace data from sequencing runs, makes base calls for assembly of cDNA sequences, produces quality scores | |
| Phrap | | Quality-score based assembly program for shotgun sequences | match > 56 score > 120 |
| CONSED | | Graphical tool for editing Phrap contigs | |
| GCG Assembly, Motifs, Profilescan, | GenBank PROSITE | Wisconsing PackagePrograms for the assembly, editing, and characterization of nucleotide sequences | |
| Spscan | | Examines proteins for secretory, signal sequences | >7 strong, 4.5–7 suggestive |
| GENEMARK | | Statistical analysis of nucleotide sequences to identify open reading frame | |
| BLAST | GenBank SwissProt | Ultra-fast database searching program for UNIX, VMS C source | score > 100, P < 1e–5 |
| FASTX | GenBank SwissProt | Fast amino acid sequence database searching program for UNIX, VMS | log likelihood > 17 |
| BLIMPS | BLOCKS PRINTS | Weighted matrix analysis for prediction of protein family | >1300 strong, 1000–1300 suggestive, P < 1e–3 |
| PFAM | PROSITE | Analyses sequences 3–60 amino acids long which correspond to highly conserved regions of a protein family | Score > 11 strong, 8–10 suggestive |
| HMM | | Probabilistic approaches and modeling of the primary structure of protein families | Score > 11 strong, 8–10 suggestive |
| McDNAsis Pro | | Software for sequence analysis | |
| LASERGENE | | Software programs (EditSeq, MegAlign, PrimerSelect, Protean, SeqMan, etc.) for sequence analysis | |

What is claimed is:

1. An isolate antibody which specifically binds with high affinity to a polypeptide comprising an amino acid sequence of SEQ ID NO:1, wherein the antibody binds to an epitope of a polypeptide consisting of the sequence of SEQ: ID NO: 1.

2. The antibody of claim 1, wherein the antibody is:
   a) a chimeric antibody,
   b) a single chain antibody,
   c) a Fab fragment,
   d) a F(ab'), fragment, or
   e) a humanized antibody.

3. A comprising an antibody of claim 1 and an acceptable excipient.

4. A of claim 3 further comprising a label.

5. A method preparing a polyclonal antibody, the method comprising:
   a) immunizing an animal with a polypeptide consisting of an amino acid sequence of SEQ ID NO:1 under conditions to elicit an antibody response,
   b) isolating antibodies from the animal, and
   c) screening the isolated antibodies with the polypeptide, thereby identifying a polyclonal antibody which specifically binds with high affinity to a polypeptide comprising an amino acid sequence of SEQ ID NO:1.

6. A polyclonal antibody produced by a method of claim 5.

7. A composition comprising the polyclonal antibody of claim 6 and a suitable carrier.

8. A method of making a monoclonal antibody, the method comprising:

a) immunizing an animal with a polypeptide consisting of an amino acid sequence of SEQ ID NO:1 under conditions to elicit an antibody response,
b) isolating antibody producing cells from the animal,
c) fusing the antibody producing cells with immortalized cells to form monoclonal antibody-producing hybridoma cells,
d) culturing the hybridoma cells, and
e) isolating from the culture a monoclonal antibody which specifically binds with high affinity to a polypeptide comprising an amino acid sequence of SEQ ID NO:1.

9. A monoclonal antibody produced by a method of claim 8.

10. A composition comprising the monoclonal antibody of claim 9 and a suitable carrier.

11. The antibody of claim 1, wherein the antibody is produced by screening a Fab expression library.

12. The antibody of claim 1, wherein the antibody is produced by screening a combinatorial immunoglobulin library.

13. A method of erecting a polypeptide comprising an amino acid sequence of SEQ ID NO:1 in a sample, the method comprising:
   a) incubating the antibody of claim 1 with the sample under conditions to allow specific binding of the antibody and the polypeptide, and
   b) detecting specific binding, wherein specific binding indicates the presence of a polypeptide comprising an amino acid sequence of SEQ ID NO:1 in the sample.

* * * * *

UNITED STATES PATENT AND TRADEMARK OFFICE
CERTIFICATE OF CORRECTION

PATENT NO. : 6,660,485 B2
DATED : December 9, 2003
INVENTOR(S) : Lal et al.

It is certified that error appears in the above-identified patent and that said Letters Patent is hereby corrected as shown below:

<u>Column 47,</u>
Line 27, "isolate" should read -- isolated --
Line 36, "F(ab')" should read -- $F(ab')_2$ --
Line 38, "A comprising" should read -- A Composition comprising --
Line 40, " A of claim" should read -- A compostion of claim --
Line 41, "A method preparing" should read -- A method of preparing --

<u>Column 48,</u>
Line 46, "A method of erecting" should read -- A method of detecting --

Signed and Sealed this

Thirteenth Day of April, 2004

JON W. DUDAS
*Acting Director of the United States Patent and Trademark Office*

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 194 amino acids
      (B) TYPE: amino acid
      (C) STRANDEDNESS: single
      (D) TOPOLOGY: linear (vii) IMMEDIATE SOURCE:
      (A) LIBRARY: ADRENOT07
      (B) CLONE: 2372794

(xi) SEQUENCE DESCRIPTION: SEQ ID NO: 1 :

Met Ser Ala Leu Trp Leu Leu Leu Gly Leu Leu Ala Leu Met Asp
            5                   10                15

```
Leu Ser Glu Ser Ser Asn Trp Gly Cys Tyr Gly Asn Ile Gln Ser
                20                  25                  30

Leu Asp Thr Pro Gly Ala Ser Cys Gly Ile Gly Arg Arg His Gly
                35                  40                  45

Leu Asn Tyr Cys Gly Val Arg Ala Ser Glu Arg Leu Ala Glu Ile
                50                  55                  60

Asp Met Pro Tyr Leu Leu Lys Tyr Gln Pro Met Met Gln Thr Ile
                65                  70                  75

Gly Gln Lys Tyr Cys Met Asp Pro Ala Val Ile Ala Gly Val Leu
                80                  85                  90

Ser Arg Lys Ser Pro Gly Asp Lys Ile Leu Val Asn Met Gly Asp
                95                 100                 105

Arg Thr Ser Met Val Gln Asp Pro Gly Ser Gln Ala Pro Thr Ser
               110                 115                 120

Trp Ile Ser Glu Ser Gln Val Ser Gln Thr Thr Glu Val Leu Thr
               125                 130                 135

Thr Arg Ile Lys Glu Ile Gln Arg Arg Phe Pro Thr Trp Thr Pro
               140                 145                 150

Asp Gln Tyr Leu Arg Gly Gly Leu Cys Ala Tyr Ser Gly Gly Ala
               155                 160                 165

Gly Tyr Val Arg Ser Ser Gln Asp Leu Ser Cys Asp Phe Cys Asn
               170                 175                 180

Asp Val Leu Ala Arg Ala Lys Tyr Leu Lys Arg His Gly Phe
               185                 190

(2) INFORMATION FOR SEQ ID NO: 2:

(i) SEQUENCE CHARACTERISTICS:
        (A) LENGTH: 1046 base pairs
        (B) TYPE: nucleic acid
        (C) STRANDEDNESS: single
        (D) TOPOLOGY: linear (vii) IMMEDIATE SOURCE:
        (A) LIBRARY: ADRENOT07
        (B) CLONE: 2372794

(xi) SEQUENCE DESCRIPTION: SEQ ID NO: 2 :

TTGCTATGTT GCCCAGGCTG GTCTTGAAGT GCCTTGACCT CCTAAAGTGT TGGAACCACA    60

GACGTGAGCC ACTCCACCCA GCCTAAAACT TCATCTTCTT TGGATGAGAT GAACACTTTT   120

AACAAGAGAA CAGGACTCTA TATAAATCGC TGTGGGCTCA CCACCTCTAA GGAGGAGCAC   180

TGACTGAAGA CAGAAAAATT GATGAACTGA AGAAGACATG GTCCATTATG CCTTACAAAC   240

TTACACAGTG CTTTGGGAAT TCCAAAGTAC TCAGTGGAGA GAGGTGTTTC AGGAGCCGTA   300

GAGCCAGATC GTCATCATGT CTGCATTGTG GCTGCTGCTG GCCTCCTTG CCCTGATGGA   360

CTTGTCTGAA AGCAGCAACT GGGGATGCTA TGGAAACATC CAAAGCCTGG ACACCCCTGG   420

AGCATCTTGT GGGATTGGAA GACGTCACGG CCTGAACTAC TGTGGAGTTC GTGCTTCTGA   480

AAGGCTGGCT GAAATAGACA TGCCATACCT CCTGAAATAT CAACCCATGA TGCAAACCAT   540

TGGCCAAAAG TACTGCATGG ATCCTGCCGT GATCGCTGGT GTCTTGTCCA GGAAGTCTCC   600

CGGTGACAAA ATTCTGGTCA ACATGGGCGA TAGGACTAGC ATGGTGCAGG ACCCTGGCTC   660

TCAAGCTCCC ACATCCTGGA TTAGTGAGTC TCAGGTTTCC CAGACAACTG AAGTTCTGAC   720

TACTAGAATC AAAGAAATCC AGAGGAGGTT TCCAACCTGG ACCCCTGACC AGTACCTGAG   780

AGGTGGACTC TGTGCCTACA GTGGGGGTGC TGGCTATGTC CGAAGCAGCC AGGACCTGAG   840
```

```
CTGTGACTTC TGCAATGATG TCCTTGCACG AGCCAAGTAC CTCAAGAGAC ATGGCTTCTA      900

ACATCTCAGA TGAAACCCAA GACCATGATC ACATATGCAG CCTCAAATGT TACACAGATA      960

AAACTAGCCA AGGGCACCTG TAACTGGGAA TCTGAGTTTG ACCTAAAAGT CATTAAAATA     1020

ACATGAATCA CATTAAAGGA AGAATT                                          1046

(2) INFORMATION FOR SEQ ID NO: 3:

(i) SEQUENCE CHARACTERISTICS:
        (A) LENGTH: 221 base pairs
        (B) TYPE: nucleic acid
        (C) STRANDEDNESS: single
        (D) TOPOLOGY: linear (vii) IMMEDIATE SOURCE:
        (A) LIBRARY: ADRENOT07
        (B) CLONE: 2372794H1

(xi) SEQUENCE DESCRIPTION: SEQ ID NO: 3 :

GGGATGCTAT GGAAACATCC AAAGCCTGGA CACCCCTGGA GCATCTTGTG GGATTGGAAG       60

ACGTCACGGC CTGAACTACT GTGGAGTTCG TGCTTCTGAA AGGCTGGCTG AAATAGACAT      120

GCCATACCTC CTGAAATATC AACCCATGAT GCAAACCATT GGCCAAAAGT ACTGCATGGA      180

TCCTGCCGTG ATCGCTGGTG TCTTGTCCAG GAAGTCTCCC G                         221

(2) INFORMATION FOR SEQ ID NO: 4:

(i) SEQUENCE CHARACTERISTICS:
        (A) LENGTH: 247 base pairs
        (B) TYPE: nucleic acid
        (C) STRANDEDNESS: single
        (D) TOPOLOGY: linear (vii) IMMEDIATE SOURCE:
        (A) LIBRARY: COLNNON03
        (B) CLONE: 3219266H1

(xi) SEQUENCE DESCRIPTION: SEQ ID NO: 4 :

TAAAACTTCA TCTTCTTTGG ATGAGATGAA CACTTTTAAC AAGAGAACAG GACTCTATAT       60

AAATCGCTGT GGGCTCACCA CCTCTAAGGA GGAGCACTGA CTGAAGACAG AAAAATTGAT      120

GAACTGAAGA AGACATGGTC CATTATGCCT TACAAACTTA CACAGTGCTT TGGGAATTCC      180

AAAGTACTCA GTGGAGAGAG GTGTTTCAGG AGCCGTAGAG CCAGATCGTC ATCATGTCTG      240

CATTGTG                                                               247

(2) INFORMATION FOR SEQ ID NO: 5:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (vii) IMMEDIATE SOURCE:
        (A) LIBRARY: ADRENOT07
        (B) CLONE: 2372794F6

(xi) SEQUENCE DESCRIPTION: SEQ ID NO: 5 :

GGGATGCTAT GGAAACATCC AAAGCCTGGA CACCCCTGGA GCATCTTGTG GGATTGGAAG       60

ACGTCACGGC CTGAACTACT GTGGAGTTCG TGCTTCTGAA AGGCTGGCTG AAATAGACAT      120

GCCATACCTC CTGAAATATC AACCCATGAT GCAAACCATT GGCCAAAAGT ACTGCATGGA      180

TCCTGCCGTG ATCGCTGGTG TCTTGTCCAG GAAGTCTCCC GGTGACAAAA TTCTGGTCAA      240
```

-continued

```
CATGGGCGAT AGGACTAGCA TGGTGCAGGA CCCTGGCTCT CAAGCTCCCA CATCCTGGAT    300

TAGTGAGTCT CAGGTTTCCC AGACAACTGA AGTTCTGACT ACTAGAATCA AAGAAATCCA    360

GAGGAGGTTT CCAACTGGAC CCCTGACCAG TACTGAGAGG TGGACTCTGT GCCTACAGTG    420

GGGGTGCTGG CTATGTTCCG AAGCAGCCAG GACCTGAGCT GTGACTTCTG CAATGATGTC    480

CTTGCACGAG CCAAGTACCT CCAAGAG                                        507
```

(2) INFORMATION FOR SEQ ID NO: 6:

(i) SEQUENCE CHARACTERISTICS:
        (A) LENGTH: 546 base pairs
        (B) TYPE: nucleic acid
        (C) STRANDEDNESS: single
        (D) TOPOLOGY: linear (vii) IMMEDIATE SOURCE:
        (A) LIBRARY: ADRENOT07
        (B) CLONE: 2372794T6

(xi) SEQUENCE DESCRIPTION: SEQ ID NO: 6 :

```
ATTCTTCCTT TAATGTGATT CATGTTATTT TAATGACTTT TAGGTCAAAC TCAGATTCCC     60

AGTTACAGGT GCCCTTGGCT AGTTTTATCT GTGTAACATT TGAGGCTGCA TATGTGATCA    120

TGGTCTTGGG TTTCATCTGA GATGTTAGAA GCCATGTCTC TTGAGGTACT TGGCTCGTGC    180

AAGGACATCA TTGCAGAAGT CACAGCTCAG GTCCTGGCTG CTTCGGACAT AGCCAGCACC    240

CCCACTGTAG GCACAGAGTC CACCTCTCAG GTACTGGTCA GGGGTCCAGG TTGGAAACCT    300

CCTCTGGATT TCTTTGATTC TAGTAGTCAG AACTTCAGTT GTCTGGGAAA CCTGAGACTC    360

ACTAATCCAG GATGTGGGAG CTTGAGAGCC AGGGTCCTGC ACCATGCTAG TCCTATCGCC    420

CATGTTGACC AGAATTTTGT CACCGGGAGA CTTCCTGGAC AAGACACCAG CGATCACGGC    480

AGGATCCATG CAGTACTTTT GGCCAATGGT TGCATCATGG GTTGATATTT CAGGAGGTAT    540

GGCATG                                                               546
```

(2) INFORMATION FOR SEQ ID NO: 7:

(i) SEQUENCE CHARACTERISTICS:
        (A) LENGTH: 211 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: GI 63428

(xi) SEQUENCE DESCRIPTION: SEQ ID NO: 7 :

```
Met Leu Gly Lys Asn Asp Pro Met Cys Leu Val Leu Val Leu Leu
                 5                  10                  15

Gly Leu Thr Ala Leu Gly Ile Cys Gln Gly Gly Thr Gly Cys
                20                  25                  30

Tyr Gly Ser Val Ser Arg Ile Asp Thr Thr Gly Ala Ser Cys Arg
                35                  40                  45

Thr Ala Lys Pro Glu Gly Leu Ser Tyr Cys Gly Val Arg Ala Ser
                50                  55                  60

Arg Thr Ile Ala Glu Arg Asp Leu Gly Ser Met Asn Lys Tyr Lys
                65                  70                  75

Val Leu Ile Lys Arg Val Gly Glu Ala Leu Cys Ile Glu Pro Ala
                80                  85                  90
```

-continued

```
Val Ile Ala Gly Ile Ile Ser Arg Glu Ser His Ala Gly Lys Ile
                 95              100                 105

Leu Lys Asn Gly Trp Gly Asp Arg Gly Asn Gly Phe Gly Leu Met
                110             115                 120

Gln Val Asp Lys Arg Tyr His Lys Ile Glu Gly Thr Trp Asn Gly
                125             130                 135

Glu Ala His Ile Arg Gln Gly Thr Arg Ile Leu Ile Asp Met Val
                140             145                 150

Lys Lys Ile Gln Arg Lys Phe Pro Arg Trp Thr Arg Asp Gln Gln
                155             160                 165

Leu Lys Gly Gly Ile Ser Ala Tyr Asn Ala Gly Val Gly Asn Val
                170             175                 180

Arg Ser Tyr Glu Arg Met Asp Ile Gly Thr Leu His Asp Asp Tyr
                185             190                 195

Ser Asn Asp Val Val Ala Arg Ala Gln Tyr Phe Lys Gln His Gly
                200             205                 210

Tyr
```